United States Patent [19]

Ono et al.

[11] 4,347,179

[45] Aug. 31, 1982

[54] PROCESS FOR THE PREPARATION OF IMMUNOGAMMAGLOBULIN USING TRITHIONATE COMPOUNDS

[75] Inventors: Syoji Ono, Kodaira; Shuzi Miura, Hino; Tsunemasa Yoshida, Hachioji, all of Japan

[73] Assignee: Teijin Limited, Osaka, Japan

[21] Appl. No.: 233,611

[22] PCT Filed: May 23, 1979

[86] PCT No.: PCT/JP79/00131

§ 371 Date: Jan. 23, 1981

§ 102(e) Date: Jan. 22, 1981

[87] PCT Pub. No.: WO80/02561

PCT Pub. Date: Nov. 27, 1980

[51] Int. Cl.³ .................. A61K 39/395; A61K 39/44; C07G 7/00
[52] U.S. Cl. .................................... 260/112 B; 424/85
[58] Field of Search .................................... 260/112 B

[56] References Cited

U.S. PATENT DOCUMENTS 4,059,571  11/1977  Tomibe et al. .................. 260/112 B

OTHER PUBLICATIONS

Chem. Abstracts, vol. 91, 1979, 145953b, Ono et al., effective date May 30, 1979.

*Primary Examiner*—Howard E. Schain
*Attorney, Agent, or Firm*—Sughrue, Mion, Zinn, Macpeak & Seas

[57] ABSTRACT

A process for the preparation of immunogammaglobulin derivatives that can be administered by intravenous injection because of their reduced anticomplement activity level in which the reaction of human immunogammaglobulin with a compound capable of forming trithionate ion and another compound capable of forming sulfite ion in water is carried out in water to cleave the interchain disulfide bonds in said immunogammaglobulin and simultaneously the sulfur atoms cleaved are S-sulfonated.

8 Claims, 4 Drawing Figures

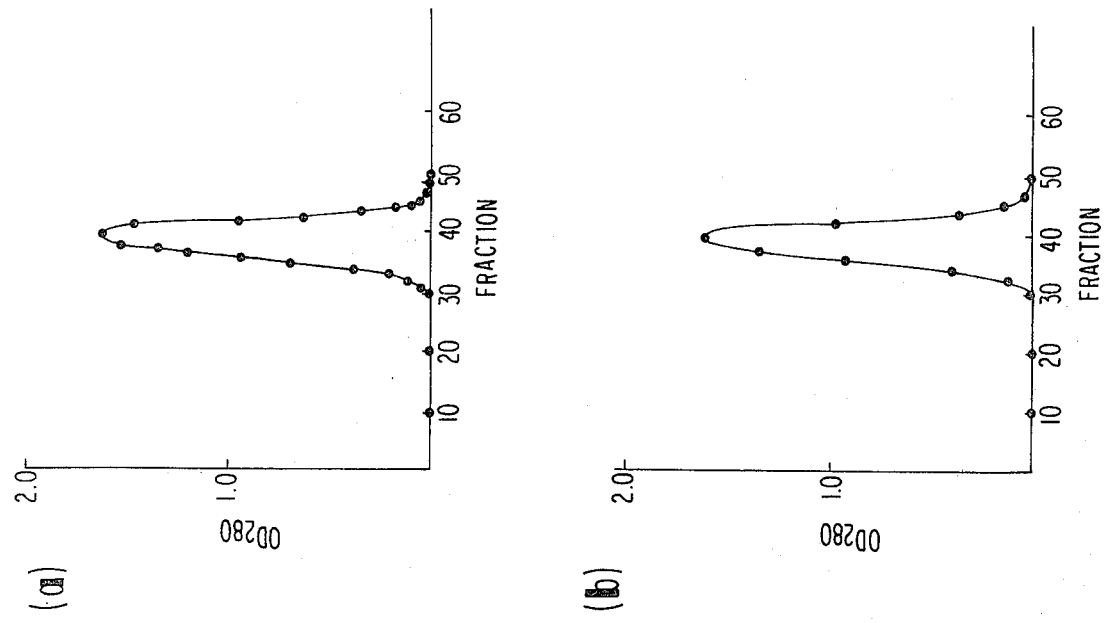
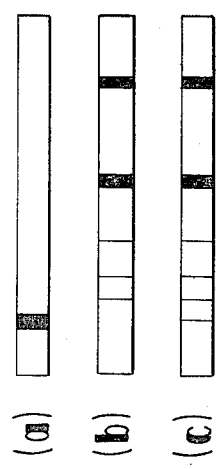
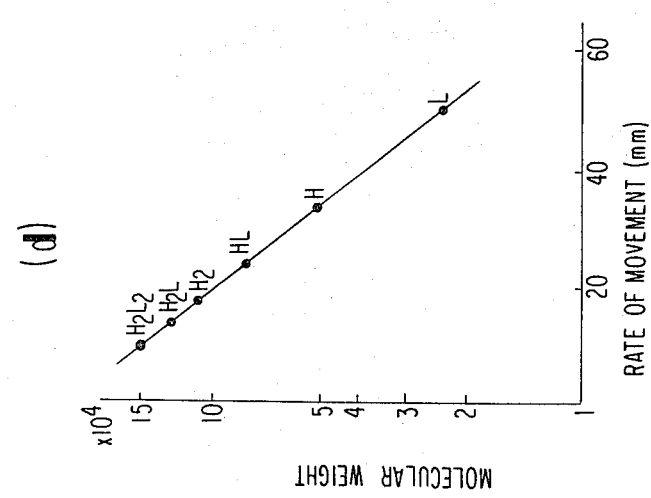
FIG. 1
FIG. 2

PROCESS FOR THE PREPARATION OF IMMUNOGAMMAGLOBULIN USING TRITHIONATE COMPOUNDS

TECHNICAL FIELD

The present invention relates to a process for the preparation of immunogammaglobulin. More particularly, the present invention relates to an improved process for the preparation of S-sulfonated immunogammaglobulin.

BACKGROUND ART

Immunoglobulin includes antibodies against a variety of diseases and is used for the prophylaxis and therapy of these diseases, however, the use of immunoglobulin preparation has been limited to intramuscular injection. Namely, when an immunoglobulin preparation is intravenously injected, the immunoglobulin binds with the complement to lower the serum complementary concentration and cause a side-effect called anticomplementary action, resulting in the observation of blood pressure drop, body temperature rise, disorder in circulatory system and others. Therefore, many studies have been made to attain the purpose of keeping immunoglobulin stable on intravenous administration.

The first method is to cut off the part that is thought to bind with the complement from human immunoglobulin by use of enzyme. For example, A. Nisonoff proposed to use pepsin as an enzyme [c.f. Science 132. 1770 (1970)] and another method using plasminogen in serum, cathepsin and others as an enzyme is described in the specification of Japanese Pat. No. 47-37529 (1972). However, these enzyme-treated immunoglobulins have defects that their half-life period is short and consequently the duration time of the efficacy is short as E. Merler and B. Jager showed in their articles of Vox Snag 13, 102 (1967) and Arch. Intora. Med. 119, 60 (1967) respectively.

The second method is to treat human immunoglobulin with a protein-acylating reagent. For example, Japanese Patent Laid-open 49-6119 (1974) described that the acylation of human immunoglobulin gave a modified immunoglobulin with reduced anticomplement activity-level. But the acylated immunoglobulin formed by this process has a danger of giving rise to antigenecity in human bodies and the administration in large amounts has been thought to be difficult.

The third method is to reduce the disulfide bonds in human immunoglobulin, followed by alkylation. For example, according to Japanese Patent Laid-open No. 48-103723 (1973), this method gave a modified immunoglobulin having the same apparent molecular weight as that of the unmodified immunoglobulin and a reduced anticomplement activity level. However, this method is a two-stepped process and the operations are considerably complicated, thus being industrially disadvantageous.

The fourth method is to S-sulfonate the interchain disulfide bonds in human immunoglobulin with tetrathionate ion and sulfite ion to give immunoglobulin derivatives suitably used for intravenous injection [c.f. Japanese Patent Laid-open Nos. 50-121421 (1975), 51-1630, 51-76418, and 51-112512 (1976)]. This method is the best in known ones. But, in this method unstable tetrathionate salt is used as an oxidant. Therefore, a large amount of the tetrathionate salt is required to promote the complete reaction, which oftentimes causes side-reactions and further produces the denaturation of the protein to inhibit the sufficient reduction in the anticomplement activity level as a defect to be improved. Further, the oxidation power of tetrathionate ion is relatively strong to have a possibility to break intrachain disulfide bonds as well as interchain disulfide bonds and sufficient caution is inconveniently required to control the reaction.

DISCLOSURE OF THE INVENTION

The present inventors focused their research of the improvement of such defects and have found that when trithionate ion, which has high stability and appropriate reactivity, and sulfite ion are together used as oxidants, interchain disulfide bonds in human immunoglobulin are cleaved and simultaneously the cleaved sulfur atoms are S-sulfonated ($-S-SO_3^-$) to prepare immunoglobulin derivatives that are suitably used for intravenous injection because of freeness of the above defects, thus attaining the present invention.

Namely, the present invention is a process for the preparation of immunoglobulin derivatives that is characterized by conducting a reaction of human immunoglobulin with a compound capable of producing trithionate ion and another compound capable of producing sulfite ion in water to cleave the interchain disulfide bonds in the human immunoglobulin and simultaneously to S-sulfonate ($-S-SO_3^-$) the cleaved sulfur atoms.

BRIEF DESCRIPTION OF THE DRAWINGS

FIGS. 1(a), (b) and (c) show patterns of electrophoretic migration of immunoglobulin (IG), sulfonated gammaglobulin (GGS) obtained in Example 1 and another sulfonated gammaglobulin obtained in the reference on dodecyl sulfonate discs respectively. FIG. 1(d) shows the relationship between each band in the above patterns and molecular weight.

FIGS. 2(a) and (b) show the gel filtration patterns of sulfonated gammaglobulin (GGS) obtained in Example 1 and another sulfonated gammaglobulin (GGS) obtained in the reference using Sephadex G 200 respectively.

BEST MODE OF CARRYING OUT THE INVENTION

Any compound can be used as a trithionate ion resource, one of the oxidants used in the present invention, if it can form trithionate ion in water, however, an alkali metal salt of trithionate such as sodium trithionate or potassium trithionate is preferred.

Any compound can be used as a sulfite ion resource, if it can form sulfite ion in water, however, a preferred example is sulforous acid, sodium sulfite, sodium bisulfite, potassium sulfite or sodium pyrobisulfite.

The amount of the compound capable of forming sulfite ion is twice or more, preferably more than 10 times the molar quantity of the interchain disulfide bonds to be cleaved in immunoglobulin. The amount of the compound capable of forming trithionate ion is more than one mole, preferably two or more moles per mole of the interchain disulfide bonds to be cleaved in immunoglobulin. The reaction is effected in water and the pH is preferably kept in the range from 6.0 to 10.0 during the reaction.

The reaction temperature is 50° C. or lower, preferably in the range from 10° to 45° C. When the temperature exceeds 50° C., the immunoglobulin molecule undesirably becomes more susceptible to protein denaturation while temperatures lower than 10° C. extremely retard the progress of the reaction, thus being industrially unpractical.

The reaction time, in which almost of the interchain disulfide bonds in immunoglobulin are cleaved and S-sulfonated, depends upon the amount of the oxidants and the reaction temperature. In general it is chosen in the range from 0.5 to 24 hours.

According to the present invention, immunoglobulin is cleaved in almost of the interchain disulfide bonds and the disulfide is converted to S-sulfonate groups (—S—SO$_3^-$) to give the H-chain and L-chain. The reaction product is separated by a usual purification method such as dialysis, salting-out or column chromatography. For example, the reaction mixture is dialyzed with normal saline solution to give the objective substance in normal saline solution.

The present invention will be further illustrated by the hereinafter presented examples. It is to be understood, however, that these examples are presented as illustrative only and that is in no way intended to limit the present invention thereto.

REFERENCE

1. Preparation of sodium trithionate

The objective compound was obtained from sodium thiosulfate and 30% aqueous hydrogen peroxide through a method described in new series of experimental chemistry ("Shin Jikken Kagaku Koza") Vol 8. Syntheses of inorganic compounds (II), P482, Maruzen Tokyo.

Substantially no change was observed when it was stood at room temperature for several months. Further, the heating of the aquous solution at 45° C. for 4.5 hours caused scarcely changes, too.

2. Preparation of sodium tetrathionate

Sodium tetrathionate was prepared from sodium thiosulfate and iodine through a method described in the Handbuch der Präparativen Anorganischen Chemie, Vol 1. p 362, Ferdinand Enke Verlag Stuttgart 1960.

The product fell to 85% in purity when stood at room temperature for one week to evolve the odor of sulfur dioxide. Further, the heating of the aqueous solution at 45° C. for 4.5 hours resulted in the reduction of purity to lower than 50%.

EXAMPLE I

A human immunoglobulin 16% concentration solution in normal saline solution that is buffered to 7.5 pH with phosphate solution (5 ml) was combined with normal saline solution (5 ml) that contains sodium sulfite (0.1616 g., 6.4 times the molar quantity of the interchain disulfide bonds in immunoglobulin) and sodium trithionate (0.076 g., 16 times the molar amount of the interchain disulfide bonds) and is buffered to 7.5 pH with phosphate solution and the reaction was effected at a temperature of 45° C. for 4.5 hours. After the completion of the reaction, the reaction mixture was dialyzed with normal saline solution until the reactants became 0.1 mMol/l or lower in concentration to obtain 11 ml of sulfonated gammaglobulin 7% concentration solution in normal saline solution.

The anticomplement activity level CH$_{50}$ was determined on the 5% solution in accordance with the method described by Kabat and Mayer (Experimental Immunochemistry, p 221, 1961) and found to be 14.9%.

The CH$_{50}$ of the 5% solution of human immunoglobulin, the starting material, was 90%.

The titre of anti-diphtheria of the product was found to be 0.8 units/ml, which was the same level as that of the human immunoglobulin, the starting material.

Further, the product was subjected to the sodium dodecylsulfonate-disc electrophoresis in accordance with a method by Weber and Osborne (J. Biol. Chem. 244, 446, 1969). The result is given as FIG. 1(b), which definitely shows that the produce is almost composed to the H-Chain and L-chain and the interchain disulfide bonds have been sulfonated.

In the meantime, the same reaction was carried out using $^{35}$S-labelled sodium sulfite to confirm that 7–8.5 moles of —S—SO$_3^-$ groups were introduced per mole of the immunoglobulin.

The pattern of immunoelectrophoresis was found to coincide entirely with that of the product obtained by use of sodium tetrathionate [c.f. FIG. 1(c)].

As a reference, the pattern of human immunogammaglobulin is given in FIG. 1(a).

Further, the gel filtration pattern using Sephadex G-200 is shown as FIG. 2(a). The OD$_{450}$ of 5% solution was found to be 0.950.

EXAMPLE II

The reaction was carried out in the same manner as in Example I except that 0.015 g. (3.2 times the molar quantity of the interchain sulfide bonds) of sodium trithionate was employed to form sulfonated gammaglobulin with anticomplement activity level CH$_{50}$ of 15.2%.

REFERENCE

A human immunoglobulin 16% concentration solution in phosphate-buffered normal saline solution (5 ml) was combined with another normal saline solution buffered to 7.5 pH with phosphate solution (5 ml) that contains sodium sulfite (0.1616 g., 64 times the molar quantity of the interchain disulfide bonds in the immunoglobulin) and sodium tetrathionate dihydrate (0.098 g., 16 times the molar quantity of the interchain disulfide bonds) and the reaction was effected at a temperature of 45° C. for 4.5 hours. After the completion of the reaction, the reaction mixture was dialyzed with normal saline solution until the concentration of the reactants became lower than 0.1 mMol/l to give 11 ml of sulfonated gammaglobulin 7% concentration solution in normal saline solution.

The anticomplement activity level CH$_5$ of the 5% solution was found to be 20.2% and OD$_{450}$ was 0.112.

The pattern of the sodium dodecylsulfate disc electrophoresis of the product is given in FIG. 1(c) and the gel filtration pattern using Sephadex G-200 is shown in FIG. 2(b).

INDUSTRIAL APPLICABILITY

In the present invention, relatively stable trithionate ion and sulfite ion are used as sulfonating reagent and undersirable decomposition of these reagents can be avoided. Thus, large amounts of the reagents become unnecessary and it leads to less side-reactions. Consequently, the present invention has advantages of giving immunogammaglobulin derivatives suitably used for intravenous injection because they have low anticomplement activity level and turbidity and can be readily purified by very simple operations.

The S-sulfonated immunogammaglobulin prepared according to the present invention returns to the original immunoglobulin in vivo and resists the decomposition in blood with no danger of producing antigenecity. Moreover, said S-sulfonated immunogammaglobulin has characteristics of enabling intravenous injection because of its reduced anticomplement activity level without any adverse effect on various kinds of antibody activities and of having very long duration period of the efficacy in vivo.

We claim:

1. A process for the preparation of immunogammaglobulin derivatives in which the reaction of human immunogammaglobulin with a compound capable of forming trithionate ion and another compound capable of forming sulfite ion in water is carried out in water to cleave interchain disulfide bonds in said immunogammaglobulin and simultaneously the sulfur atoms cleaved are S-sulfonated ($-S-SO_3^-$).

2. A process for the preparation of immunoglobulin derivatives according to claim 1 wherein the compound capable of forming trithionate ion in water is one selected from sodium trithionate, potassium trithionate or their mixture.

3. The process of claims 1 or 2, wherein said compound capable of forming trithionate ion is present in an amount greater than 1 mol/mol of said disulfide bonds to be cleaved and said compound capable of forming sulfite ion is present in an amount of at least 2 mol/mol of said interchain disulfide bonds to be cleaved.

4. The process of claim 3, wherein said trithionate ion forming compound is present in an amount of 2 or more mols/mol of said interchain disulfide bonds to be cleaved, and said sulfite ion forming compound is present in an amount exceeding 10 mols/mol interchain disulfide bond to be cleaved.

5. The process of claims 1 or 2, wherein the pH of the reaction mixture is maintained in the range of from 6.0–10.0.

6. The process of claims 1 or 2, wherein the reaction temperature is maintained at 50° C. or less.

7. The process of claims 1 or 2, wherein the reaction temperature is maintained in the range of 10° C.–45° C.

8. The process of claim 4, wherein the pH of the reaction mixtures maintained at 6.0–10.0 and the reaction temperature is maintained in the range of from 10° C.–45° C.

* * * * *